(12) United States Patent
Steinmetz et al.

(10) Patent No.: US 10,098,936 B2
(45) Date of Patent: Oct. 16, 2018

(54) VACCINATION USING PLANT VIRUS PARTICLES LINKED TO HER2 ANTIGENS

(71) Applicant: CASE WESTERN RESERVE UNIVERSITY, Cleveland, OH (US)

(72) Inventors: Nicole F. Steinmetz, Cleveland, OH (US); Sourabh Shukla, Cleveland, OH (US)

(73) Assignee: Case Western Reserve University, Cleveland, OH (US)

(*) Notice: Subject to any disclaimer, the term of this patent is extended or adjusted under 35 U.S.C. 154(b) by 26 days.

(21) Appl. No.: 15/300,931

(22) PCT Filed: Apr. 2, 2015

(86) PCT No.: PCT/US2015/024086
§ 371 (c)(1),
(2) Date: Sep. 30, 2016

(87) PCT Pub. No.: WO2015/153883
PCT Pub. Date: Oct. 8, 2015

(65) Prior Publication Data
US 2017/0021003 A1    Jan. 26, 2017

Related U.S. Application Data

(60) Provisional application No. 61/974,053, filed on Apr. 2, 2014.

(51) Int. Cl.
| | |
|---|---|
| *C07H 21/04* | (2006.01) |
| *C12N 15/82* | (2006.01) |
| *C12N 15/11* | (2006.01) |
| *A61K 48/00* | (2006.01) |
| *A01H 1/00* | (2006.01) |
| *A61K 39/00* | (2006.01) |
| *C07K 14/005* | (2006.01) |
| *C12N 7/00* | (2006.01) |

(52) U.S. Cl.
CPC ........ *A61K 39/0011* (2013.01); *C07K 14/005* (2013.01); *C12N 7/00* (2013.01); *A61K 2039/5258* (2013.01); *A61K 2039/54* (2013.01); *A61K 2039/542* (2013.01); *C12N 2770/26023* (2013.01); *C12N 2770/26043* (2013.01); *C12N 2770/26071* (2013.01)

(58) Field of Classification Search
CPC ................ C12N 15/1037; C40B 40/02; G01N 33/5005; G01N 33/543; G01N 33/5432
See application file for complete search history.

(56) References Cited

U.S. PATENT DOCUMENTS

2012/0195962 A1    8/2012 Krammer et al.

FOREIGN PATENT DOCUMENTS

| WO | 2012155262 A1 | 11/2012 |
| WO | WO2012155262 | * 11/2012 |
| WO | WO2014/139672 | * 9/2014 |

OTHER PUBLICATIONS

Jasinska et al., Int. J. Cancer, 2003, 107:976-983.*
Steinmetz et al., Nano Letters, 2010, 10:305-312.*
Oyston and Robinson, Journal of Medical Microbiology, 2012, 61:889-894.*
Jasinska, Joanna, et al. "Inhibition of tumor cell growth by antibodies induced after vaccination with peptides derived from the extracellular domain of Her-2/neu." International journal of cancer 107.6 (2003): 976-983.
PCT International Search Report and Written Opinion for PCT/US2015/024086, dated Jul. 13, 2015, pp. 1-9.

* cited by examiner

*Primary Examiner* — Barry A Chestnut
(74) *Attorney, Agent, or Firm* — Tarolli, Sundheim, Covell & Tummino LLP

(57) ABSTRACT

A vaccine composition including a plant virus particle linked to an HER2 antigen is described. The vaccine composition can be used for methods of treating or preventing an HER2-expressing cancer in a subject by administering to a subject in need thereof an effective amount of the vaccine composition.

12 Claims, 6 Drawing Sheets

Specification includes a Sequence Listing.

SEQUENCE LISTING

<160> NUMBER OF SEQ ID NOS: 12

<210> SEQ ID NO 1
<211> LENGTH: 21
<212> TYPE: PRT
<213> ORGANISM: Homo sapiens

<400> SEQUENCE: 1

Pro Glu Ser Phe Asp Gly Asp Pro Ala Ser Asn Thr Ala Pro Leu Gln
1               5                   10                  15

Pro Glu Gln Leu Gln
            20

<210> SEQ ID NO 2
<211> LENGTH: 21
<212> TYPE: PRT
<213> ORGANISM: Artificial Sequence
<220> FEATURE:
<223> OTHER INFORMATION: P4 HER2 antigen including glycine and cysteine
      linker

<400> SEQUENCE: 2

Pro Glu Ser Phe Asp Gly Asp Pro Ala Ser Asn Thr Ala Pro Leu Gln
1               5                   10                  15

Pro Gly Gly Gly Cys
            20

<210> SEQ ID NO 3
<211> LENGTH: 24
<212> TYPE: PRT
<213> ORGANISM: Homo sapiens

<400> SEQUENCE: 3

Pro Leu His Asn Gln Glu Val Thr Ala Glu Asp Gly Thr Gln Arg Ala
1               5                   10                  15

Glu Lys Cys Ser Lys Pro Cys Ala
            20

<210> SEQ ID NO 4
<211> LENGTH: 19
<212> TYPE: PRT
<213> ORGANISM: Homo sapiens

<400> SEQUENCE: 4

Leu Phe Arg Asn Pro His Gln Ala Leu Leu His Thr Ala Asn Arg Pro
1               5                   10                  15

Glu Asp Glu

<210> SEQ ID NO 5
<211> LENGTH: 18
<212> TYPE: PRT
<213> ORGANISM: Homo sapiens

<400> SEQUENCE: 5

Lys Pro Asp Leu Ser Tyr Met Pro Ile Trp Lys Phe Pro Asp Glu Glu
1               5                   10                  15

Gly Ala

<210> SEQ ID NO 6
<211> LENGTH: 20
<212> TYPE: PRT
<213> ORGANISM: Homo sapiens

<400> SEQUENCE: 6

Ile Asn Gly Thr His Ser Cys Val Asp Leu Asp Asp Lys Gly Cys Pro
1               5                   10                  15

Ala Glu Gln Arg
            20

<210> SEQ ID NO 7
<211> LENGTH: 17
<212> TYPE: PRT
<213> ORGANISM: Homo sapiens

<400> SEQUENCE: 7

Cys Arg Val Leu Gln Gly Leu Pro Arg Glu Tyr Val Asn Ala Arg His
1               5                   10                  15

Cys

<210> SEQ ID NO 8
<211> LENGTH: 14
<212> TYPE: PRT
<213> ORGANISM: Homo sapiens

```
<400> SEQUENCE: 8

Tyr Met Pro Ile Trp Lys Phe Pro Asp Glu Glu Gly Ala Cys
1               5                   10

<210> SEQ ID NO 9
<211> LENGTH: 18
<212> TYPE: PRT
<213> ORGANISM: Homo sapiens

<400> SEQUENCE: 9

Tyr Gln Asp Thr Ile Leu Trp Lys Asp Ile Phe His Lys Asn Asn Gln
1               5                   10                  15

Leu Ala

<210> SEQ ID NO 10
<211> LENGTH: 46
<212> TYPE: PRT
<213> ORGANISM: Homo sapiens

<400> SEQUENCE: 10

Lys Leu Leu Ser Leu Ile Lys Gly Val Ile Val His Arg Leu Glu Gly
1               5                   10                  15

Val Glu Gly Pro Ser Leu Cys Pro Ile Asn Cys Thr His Ser Cys Val
                20                  25                  30

Asp Leu Asp Asp Lys Gly Cys Pro Ala Glu Gln Arg Ala Ser
            35                  40                  45

<210> SEQ ID NO 11
<211> LENGTH: 36
<212> TYPE: PRT
<213> ORGANISM: Homo sapiens

<400> SEQUENCE: 11

Cys His Pro Glu Cys Gln Pro Gln Asn Gly Ser Val Thr Cys Phe Gly
1               5                   10                  15

Pro Glu Ala Asp Gln Cys Val Ala Cys Ala His Tyr Lys Asp Pro Pro
                20                  25                  30

Phe Cys Val Ala
            35

<210> SEQ ID NO 12
<211> LENGTH: 30
<212> TYPE: PRT
<213> ORGANISM: Homo sapiens

<400> SEQUENCE: 12

Val Ala Arg Cys Pro Ser Gly Val Lys Pro Asp Leu Ser Tyr Met Pro
1               5                   10                  15

Ile Trp Lys Phe Pro Asp Glu Glu Gly Ala Cys Gln Pro Leu
                20                  25                  30
```

VACCINATION USING PLANT VIRUS PARTICLES LINKED TO HER2 ANTIGENS

CONTINUING APPLICATION DATA

This application claims the benefit of U.S. Provisional Application Ser. No. 61/974,053 filed Apr. 2, 2014, which is incorporated by reference herein.

SEQUENCE LISTING

The instant application contains a Sequence Listing which has been submitted in ASCII format via EFS-Web and is hereby incorporated by reference in its entirety. Said ASCII copy, created on Apr. 1, 2015, is named HER2 virus particle vaccine CWR-023274 WO ORD_ST25 and is 3,700 bytes in size.

BACKGROUND

Approximately 200,000 women will be diagnosed with breast cancer this year and more than 40,000 of those will die from the disease. About 25-30% of breast cancer patients overexpress the human epidermal growth factor receptor 2 (HER2/neu/ErbB2). HER2 has been linked to poor prognosis, high rate of metastasis, high risk of relapse, resistance to chemotherapy or hormone replacement therapies, and rapid progression to death. Ross J S, Fletcher J A, The Oncologist; 3:237-52 (1998). Trastuzumab (Herceptin) is a humanized monoclonal antibody that binds HER2 with high affinity. Passive immunotherapy with trastuzumab has dramatically improved outcomes for HER2-positive breast cancer patients. Dawood et al., J Clin Oncol.; 28:92-8A (2010). A limitation of immunotherapy with trastuzumab is the short half-life requiring frequent administration. Furthermore, passive immunotherapy with trastuzumab does not protect patients from development of metastasis or recurrence. To overcome the challenges of passive immunotherapy, cancer vaccines are under development and clinical testing. Disis et al., Immunology, 93:192-9 (1998); Nanda N K, Sercarz E E, Cell, 82:13-7 (1995).

HER2 cancer vaccines have several advantages compared to passive immunotherapy. Ladjemi et al., Cancer immunology, immunotherapy: CII, 59:1295-312 (2010). Establishment of a memory immune response could overcome resistance to passive immunotherapies upon repeated usage. A cancer vaccine holds the promise to prevent recurrence of the disease or progression to metastatic disease. Administration of a prophylactic vaccine (in high risk groups) has the potential to prevent the development of the disease before doctors would be able to diagnose its onset. Lastly, cancer vaccines offer practical advantages such as lower costs based on a less intensive treatment schedule.

While T cell and antibody-mediated immunity specific to HER2 exists in some patients, the majority of patients show immune self-tolerance to HER2 due to its fetal origin. Seliger B, Kiessling R. Trends in molecular medicine, 19:677-84 (2013). The HER2 protein, like most other tumor-associated antigens, represents an overexpressed or abnormally expressed gene product. Tolerance to such self-gene products is often mediated by many different mechanisms, with one being depletion of reactive high-avidity T cells against the antigen. T cell depletion through self-tolerance is not absolute, and reactive low-avidity T cells may be present; immunotherapeutic approaches are based on the ability to involve these low-avidity T cells in anti-cancer immunity though activation and expansion. Morgan et al., J Immunol., 160:643-51 (1998). HER2 immunogenicity is also impaired by abnormally low surface (major histocompatibility complex) MHC-I expression on tumor cells that limits or abolishes immune recognition by reactive cytotoxic T lymphocytes (CTLs) Immunotherapy outcomes could be improved by overcoming resistance arising from low MHC-I expression by approaches involving innate immunity mediated via antibody dependent cytotoxicity (ADCC) with natural killer (NK) cells and monocytes playing key roles. Musolino et al., J Clin Oncol, 26:1789-96 (2008). This mechanism is relevant to both passive antibody therapy (e.g. trastuzumab) and active vaccination approaches targeting humoral immunity. Triulzi et al., Cancer research, 70:7431-41 (2010).

Many different strategies have been proposed to overcome self-tolerance associated with the HER2 self-antigen, including depletion of regulatory T cells (Weiss et al., PLoS One. 2012; 7:e31962), altering the natural antigen to enhance immunogenicity, or presenting antigenic HER2 epitopes to the host in an altered molecular environment (foreign to the host). Disis et al., Journal of immunology, 156:3151-8 (1996). Approaches include vaccines based on proteins, peptides (Ladjemi et al., Cancer immunology, immunotherapy: CII. 2010; 59:1295-312), DNA (Radkevich-Brown et al., Cancer research. 2009; 69:212-8), anti-idiotype antibodies (de Cerio et al., Oncogene. 2007; 26:3594-602), autologous cells, dendritic cells (Saha A, Chatterjee S K., Cellular immunology. 2010; 263:9-21), and tumor cells. Dols et al., Journal of immunotherapy. 2003; 26:163-70.

Peptide-based vaccines constitute the largest group of cancer vaccines under preclinical and clinical evaluation. Several HER2 peptides derived from the extracellular domain (Mittendorf et al., Cancer immunology, immunotherapy: CII. 2008; 57:1511-21), transmembrane domain (Mittendorf et al., Cancer. 2006; 106:2309-17) or intracellular domains (Disis et al., Journal of clinical oncology, 2004; 22:1916-25) are in clinical trials as single-epitope or in combinations as multi-epitope vaccines. Several approaches have been shown to generate a HER2-specific response mediated by CTLs (cellular immunity) and/or humoral immunity. Dakappagari et al., Journal of immunology. 2003; 170:4242-53; Jasinska et al., Int J Cancer. 2003; 107:976-83. Nevertheless, peptide-based vaccines suffer from weak and short-lived immunogenicity and are dependent on adjuvants. In the absence of suitable adjuvants the peptides are prone to proteolytic degradation resulting in shorter circulation times. Thus, there is a need for improved vectors and epitope presentation strategies to develop stable peptide-based vaccines.

Antigen presentation systems (De Temmerman et al., Drug discovery today. 2011; 16:569-82; Bramwell V W, Perrie Y., Journal of Pharmacy and Pharmacology. 2006; 58:717-28), including virus-based platforms, emulsions, liposomes, as well as gel formulations, protect the antigen against proteolytic degradation, facilitate uptake by antigen-presenting cells (APCs) through passive or active targeting, and allow for co-delivery of antigens. Krishnamachari Y, Salem A K, Advanced drug delivery reviews, 61:205-17 (2009). Further, reports indicate that generation of tumor antigen-specific CTLs requires cross-priming of tumor antigens by APCs. Ridge et al., Nature, 393:474-8 (1998). Therefore, antigen delivery via virus-based platforms, which naturally interact with APCs thereby enhancing antigen delivery, may be an advantageous strategy for the development of cancer vaccines. While uptake of soluble antigen is primarily mediated by endocytosis, particulate vaccines are internalized through phagocytosis into phagosomes and thus are presented on MHC class II. Howland S W, Wittrup K D., Journal of immunology, 180:1576-83 (2008). Large quantities of antigens can be delivered, and a prolonged extracellular or intracellular release will foster prolonged antigen presentation by APCs. Shen et al., Immunology, 117:78-88 (2006).

Plant virus-based vectors displaying antigenic peptides fused to the coat proteins can be readily purified, and presentation of multiple copies of antigen on a macromolecular assembly can significantly enhance the immunogenicity of these epitopes. Jegerlehner et al., Vaccine, 20:3104-12 (2002). Several chimeric platforms have been shown to elicit protective immunity in diverse hosts in preclinical settings. Canizares et al., Immunology and cell biology, 83:263-70 (2005). PVX-based vaccine formulations have been developed and tested, for example: PVX-gp41 displaying HIV-1 epitopes (Marusic et al., Journal of Virology. 2001; 75:8434-9), PVX-R9 displaying hepatitis C virus (HCV) epitopes (Uhde-Holzem et al., Journal of virological methods. 2010; 166:12-20), PVX-*Staphylococcus aureus* D2 FnBP (Brennan et al., Vaccine, 1999; 17:1846-57), PVX-influenza-A virus nucleoprotein epitopes (Lico et al., Vaccine, 2009; 27:5069-76), and PVX-16E7 formulations displaying human papillomavirus (HPV) epitopes (Massa et al., Human gene therapy, 2008; 19:354-64). Immunization studies have shown that cellular and humoral immune responses can be triggered and epitope-specific antibodies were generated, demonstrating the utility of PVX as a presentation strategy.

SUMMARY

The inventors have developed a plant virus platform, specifically the plant viral vector, potato virus X (PVX) as an epitope presentation platform.

In particular, the inventors sought to develop and test a PVX-based HER2 vaccination platform. Specifically, the $P4_{378-394}$ B-cell epitope from the extracellular domain of HER2 (PESFDGDPASNTAPLQPEQLQ; SEQ ID NO: 1) was displayed through chemical fusion on PVX. Others have previously shown in preclinical studies that immunization with $P4_{378-394}$ epitopes as single epitope or multi-epitope formulations induced HER2-specific IgG antibodies with strong anti-tumor activity. Furthermore, a clinical phase I study using a virosomal formulated multi-epitope vaccine, containing the $P4_{378-394}$ epitope, indicated that the vaccine was safe, well tolerated, and effective in overcoming immunological tolerance to HER2. Wagner et al., Breast Cancer Res Treat. 2007; 106:29-38; Wiedermann et al., Breast Cancer Res Treat. 2009; 119:673-83. The inventors therefore chose the $P4_{378-394}$ epitope for their studies. PVX particles were produced in plants and subsequently modified with P4 via chemical ligation Immunization of healthy FVB/N mice yielded HER2-specific IgG antibodies; reactivity toward HER2 on human cancer cells was demonstrated.

DETAILED DESCRIPTION

Figure 1:
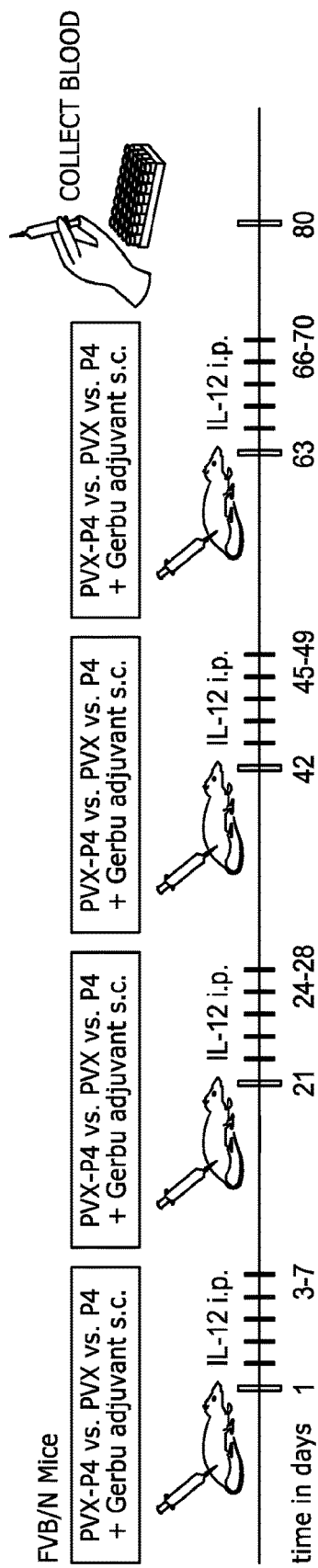
FIG. 1 provides a schematic representation of the immunization schedule used to produce an immune response using PVX-P4 filaments.

The present invention provides a vaccine composition including a plant virus particle linked to an HER2 antigen. The vaccine composition can be used for methods of treating or preventing an HER2-expressing cancer in a subject by administering to a subject in need thereof an effective amount of the vaccine composition.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

Definitions

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

As used herein, the terms "peptide," "polypeptide" and "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "nucleic acid" refers to a polynucleotide and includes polyribonucleotides and polydeoxyribonucleotides.

The term "adjuvant" as used herein, refers to an agent that augments, stimulates, potentiates and/or modulates an immune response in an animal. An adjuvant may or may not have an effect on the immune response in itself. Examples of adjuvants include muramyl dipeptide, Gerbu, and monophosphoryl lipid A.

The terms "immunogen", "antigen" and "antigenic peptide (epitope)" as used herein refer to a portion or portions of molecules which are capable of inducing a specific immune response in a subject alone or in combination with an adjuvant. An epitope generally represents a portion of an antigen.

The term "immune response", as used herein, refers to an alteration in the reactivity of the immune system of an animal in response to an antigen or antigenic material and may involve antibody production, induction of cell-mediated immunity, complement activation, development of immunological tolerance, or a combination thereof.

The term "immunoprotection" as used herein, mean an immune response that is directed against one or more antigen so as to protect against disease and/or infection by a pathogen in a vaccinated animal. For purposes of the present invention, protection against disease includes not only the absolute prevention of the disease, but also any detectable reduction in the degree or rate of disease, or any detectable reduction in the severity of the disease or any symptom in the vaccinated animal as compared to an unvaccinated infected or diseased animal Immunoprotection can be the result of one or more mechanisms, including humoral and/or cellular immunity.

The term "vaccine", as used herein, refers to a material capable of producing an immune response after being administered to a subject.

"Treating", as used herein, means ameliorating the effects of, or delaying, halting or reversing the progress of a disease or disorder. The word encompasses reducing the severity of a symptom of a disease or disorder and/or the frequency of a symptom of a disease or disorder.

A "subject", as used therein, can be a human or non-human animal. Non-human animals include, for example, livestock and pets, such as ovine, bovine, porcine, canine, feline and murine mammals, as well as reptiles, birds and fish. Preferably, the subject is human.

The language "effective amount" or "therapeutically effective amount" refers to a nontoxic but sufficient amount of the composition used in the practice of the invention that is effective to provide effective vaccination or treatment in a subject. That result can be reduction and/or alleviation of the signs, symptoms, or causes of a disease or disorder, or any other desired alteration of a biological system. An appropriate effective amount for a subject may be determined by one of ordinary skill in the art using routine experimentation.

A "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder. Use of a vaccine in a preventive treatment provides immunoprotection.

A "therapeutic" treatment is a treatment administered to a subject who exhibits signs of pathology of a disease or disorder such as cancer for the purpose of diminishing or eliminating those signs.

"Pharmaceutically acceptable carrier" refers herein to a composition suitable for delivering an active pharmaceutical ingredient, such as the vaccine composition of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

In one aspect, the present invention provides a vaccine composition comprising a plant virus particle linked to an HER2 antigen. In some embodiments, the vaccine composition also includes a pharmaceutically acceptable carrier, while in further embodiments the vaccine composition also includes an adjuvant.

Plant Virus Particles

Use of plant virus particles in the present invention is preferred because viruses from plant sources is that they can be readily cultivated, and are unlikely to cause infection when used in vivo in a subject. Plant viruses are those that infect plants. A wide variety of different types of plant viruses are known to those skilled in the art. Preferably, the virus particles used are non-enveloped virus particles. Examples of suitable plant virus particles include rod-shaped plant virus particles and icosahedral plant virus particles. Examples of rod-shaped plant viruses include tobaviruses such as tobacco mosaic virus, Alphaflexiviridae such as potato virus X, and Potyviridae such as potato virus Y. A subset of rod-shaped plant viruses are filamentous plant viruses. Examples of icosahedral viruses include plant Picornaviruses (e.g., as cowpea mosaic virus), as well as various other plant viruses such as brome mosaic virus, cowpea chlorotic mottle virus, etc.

Potato virus X (PVX) is a filamentous RNA plant virus which belongs to the Alphaflexiviridae family. One genus of the Alphaflexiviridae family is the genus Potexvirus. Potexvirus particles are non-enveloped, flexuous and filamentous, 470-1000 nm long and 12-13 nm wide, and consist of 1000-1500 copies of a coat protein subunits and one single-stranded RNA genome. Their genome is linear, 5.9-7 kilobases in length with a capped 5' end and a polyadenylated 3' end. The genome encodes 5 proteins. These proteins are the viral replication protein that consists of a capping enzyme domain, a helicase-like domain, the RNA dependent RNA polymerase, three proteins—the triple gene block (TGB) 1, 2 and 3—and the coat protein. The coat protein has a molecular weight of ~25 kDa.

In some embodiments, the plant virus particle of the vaccine composition is an Alphaflexiviridae virus particle. The genera comprising the Alphaflexiviridae family include Allexivirus, Botrexvirus, Lolavirus, Mandarivirus, Potexvirus, and Sclerodarnavirus. In further embodiments, the plant virus particle of the vaccine composition is a Potexvirus particle. Examples of Potexvirus include Allium virus X, Alstroemeria virus X, Alternanthera mosaic virus, Asparagus virus 3, Bamboo mosaic virus, Cactus virus X, Cassava common mosaic virus, Cassava virus X, Clover yellow mosaic virus, Commelina virus X, Cymbidium mosaic virus, Daphne virus X, Foxtail mosaic virus, Hosta virus X, Hydrangea ringspot virus, Lagenaria mild mosaic virus, Lettuce virus X, Lily virus X, Malva mosaic virus, Mint virus X, Narcissus mosaic virus, Nerine virus X, Opuntia virus X, Papaya mosaic virus, Pepino mosaic virus, Phaius virus X, Plantago asiatica mosaic virus, Plantago severe mottle virus, Plantain virus X, Potato aucuba mosaic virus, Potato virus X, Schlumbergera virus X, Strawberry mild yellow edge virus, Tamus red mosaic virus, Tulip virus X, White clover mosaic virus, and Zygocactus virus X. In some embodiments, the plant virus particle of the vaccine composition is a Potato virus X virus particle.

Use of the terms "virus" and "virus particle" are used interchangeably herein. Virus particles include a number of capsid proteins that are assembled to form a protein cage, within which is typically the nucleic acid encoding the virus. Note that the viruses and virus particles described herein are presumed to include a nucleic acid within the protein cage, unless specifically stated to the contrary. However, the presence of a nucleic acid within the virus is not required for compositions and methods of the present invention.

HER2 Antigen

Vaccine compositions of the present invention also include an HER2 antigen. HER2 antigens are a portion of the HER2/neu protein (also referred to herein as the HER2 protein) which are recognized by the immune system; e.g., by antibody binding. The HER2/neu proto-oncogene is expressed in breast cancer and other human cancers, and encodes a tyrosine kinase with homology to epidermal growth factor receptor. HER2/neu protein is a receptor-like transmembrane protein comprising a large cysteine-rich extracellular domain that functions in ligand binding, a short transmembrane domain, and a small cytoplasmic domain. HER2/neu is amplified and expressed in many human cancers, largely adenocarcinomas of breast, ovary, colon, and lung. In breast cancer, HER2/neu over-expression is associated with aggressive disease and is an independent predictor of poor prognosis. The HER2 protein is intimately associated with the malignant phenotype and with the aggressiveness of the malignancy, especially in breast and ovarian carcinomas. An advantage of presenting the HER2 antigen linked to a plant virus particle is that such linked particles are capable of stimulating an immune response without having to be co-administered with an adjuvant.

The present invention includes use of any HER2 antigen capable of eliciting an immune response. Examples of HER2 antigens are described in US Patent Publication 2015/0071927, U.S. Pat. No. 7,446,185, Jasinska et al., Int. J. Cancer 107, 976-983 (2003), and Wagner et al., Breast Cancer Res. Treat., 106, 29-38 (2007), the disclosures of which are incorporated herein by reference. Preferably, the HER2 antigen is a portion of the extracellular domain of the HER2 protein. A number of HER2 antigens found in the extracellular domain are listed below in table I. In other embodiments, the HER2 antigen comprises all or a portion of a P4 protein, a P6 protein, or a P7 protein, all of which form parts of the HER2 protein.

TABLE I

| HER2 antigens found in the extracellular domain | |
|---|---|
| Epitope | Amino Acid Sequence |
| ECD 316-339 | PLHNQEVTAEDGTQRAEKCS KPCA (SEQ ID NO: 3) |
| ECD 485-503 | LFRNPHQALLHTANRPEDE (SEQ ID NO: 4) |
| ECD 605-622 | KPDLSYMPIWKFPDEEGA (SEQ ID NO: 5) |
| ECD 628-647 | INGTHSCVDLDDKGCPAEQR (SEQ ID NO: 6) |
| ECD P4 378-398 | PESFDGDPASNTAPLQPEQL Q (SEQ ID NO: 1) |
| ECD P6 544-560 | CRVLQGLPREYVNARHC (SEQ ID NO: 7) |
| ECD P7 610-623 | YMPIWKFPDEEGAC (SEQ ID NO: 8) |
| ECD 163-182 | YQDTILWKDIFHKNNQLA (SEQ ID NO: 9) |
| ECD 626-649 | KLLSLIKGVIVHRLEGVEGP SLCPINCTHSCVDLDDKGCP AEQRAS (SEQ ID NO: 10) |
| ECD 563-598 | CHPECQPQNGSVTCFGPEAD QCVACAHYKDPPFCVA (SEQ ID NO: 11) |
| ECD 597-626 | VARCPSGVKPDLSYMPIWKF PDEEGACQPL (SEQ ID NO: 12) |

The epitopes in Table I are listed by their position in the extracellular domain (ECD) and in some cases by the sub-protein that they are found in.

HER2 antigens can be modified in ways that do not interfere with their ability to generate an immune reaction. For example, HER2 antigens can contain, for example, one or more D-amino acids in place of a corresponding L-amino acid; or can contain one or more amino acid analogs, for example, an amino acid that has been derivatized or otherwise modified at its reactive side chain. Similarly, one or more peptide bonds in the HER2 antigen can be modified, or a reactive group at the amino terminus or the carboxy terminus or both can be modified. Such modified HER2 antigens can have improved stability to a protease, an oxidizing agent or other reactive material the polypeptide may encounter in a living subject.

Linking the HER2 Antigen to the Plant Virus Particle

The HER2 antigen(s) can be linked to the plant virus particle in various different ways known to those skilled in the art for linking together a peptide and a protein. In some embodiments, a plurality of HER2 antigens are linked to the plant virus particle. The number of antigens linked to the plant virus particle will vary depending on the number of coat proteins in the virus particle, and the availability of suitable reactive groups (e.g., amine, carboxyl, thiol) in the coat proteins. In some embodiments, the virus particle is linked to from 2 to 1,000 HER2 antigens, while in other embodiments the virus particle is linked to from 100 to 1,000 HER2 antigens, or from 400 to 800 HER2 antigens.

In some embodiments, the HER2 antigen is connected to the plant virus particle using a linker molecule. HER2 antigens are coupled to the virus particle using a linker group. HER2 antigens can be conjugated to the plant virus particle by any suitable technique, with appropriate consideration of the need for pharmacokinetic stability and reduced overall toxicity to the patient. A linker group can serve to increase the chemical reactivity of a substituent on either the agent or the virus particle, and thus increase the coupling efficiency, and can also improve the immunogenicity of the linked antigen. In some cases, the linker can also include a short spacer consisting of 2 to 10 amino acids (e.g., glycine). Coupling can be affected, for example, through amino groups, carboxyl groups, sulfhydryl groups or oxidized carbohydrate residues. A preferred group suitable as a site for attaching antigens to the virus particle is lysine residues present in the viral coat protein.

Suitable linkage chemistries include maleimidyl linkers and alkyl halide linkers and succinimidyl (e.g., N-hydroxysuccinimidyl (NHS)) linkers (which react with a primary amine on the plant virus particle). Cysteine modified antigenic peptides using amine-to-sulfhydryl crosslinkers with aliphatic spacers that differ in chain lengths from 4.4 Angstrom to 9.4 Angstroms or crosslinkers with a PEG spacer varying in lengths form 17.6 Angstroms to 95.2 Angstroms, can also be used. Several primary amine, sulfhydryl groups, and carboxylate or tyrosine groups are present on viral coat proteins, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, Ill.), can be employed as a linker group.

In other embodiments, the HER2 antigen is linked to the plant virus particle through expression of a recombinant protein in plants using an N-terminal fusion on the coat protein. Methods for the preparation and isolation of recombinant fusion proteins are well-known to those skilled in the art. In some embodiments, the HER2 antigen is an antigen selected from Table I. For example, in one embodiment, the recombinant polypeptide includes a HER2 antigen having an amino acid sequence corresponding to amino acid residues about 378 to 398 of the P4 protein of the extracellular domain of HER2 (i.e., SEQ ID NO:1). A recombinant polypeptide of the invention can be expressed from a recombinant polynucleotide or can be chemically synthesized. Preparation of recombinant proteins including HER2 antigens is described in U.S. Pat. No. 7,446,185.

Vaccination and Cancer Treatment

In another aspect, the present invention provides a method of treating or preventing an HER2-expressing cancer in a subject, by administering to a subject in need thereof an effective amount of a vaccine composition comprising a plant virus particle linked to an HER2 antigen.

The term "cancer" as used herein, includes any malignant tumor including, but not limited to, carcinoma and sarcoma. Cancer arises from the uncontrolled and/or abnormal division of cells that then invade and destroy the surrounding tissues. As used herein, "proliferating" and "proliferation" refer to cells undergoing mitosis. As used herein, "metastasis" refers to the distant spread of a malignant tumor from its sight of origin. Cancer cells may metastasize through the bloodstream, through the lymphatic system, across body cavities, or any combination thereof. The term "cancerous cell" as provided herein, includes a cell afflicted by any one of the cancerous conditions provided herein. Thus, the methods of the present invention include treatment of cancers such as breast, ovary, recto-colon, lung, prostate, stomach, pancreatic, and biliary cancers, all of which are HER2 expressing. The term "carcinoma" refers to a malignant new growth made up of epithelial cells tending to infiltrate surrounding tissues, and to give rise to metastases. A preferred type of cancer for treatment with the vaccine compositions of the present invention is HER2-expressing cancer, and in particular HER2-overexpressing cancer. HER2 expression refers to the expression of HER2 protein on the surface of the cell, where it can be recognized by the immune system. Another preferred type of cancer for treatment with the vaccine compositions is breast cancer.

The present invention provides methods of stimulating an immune response in a subject against cells that express HER2 antigen. The cells that express HER2 can be cancer cells or any other cells that express HER2, particularly cells involved in a pathologic condition. The disclosed methods are particularly useful for stimulating an immune response against cells that are involved in a pathologic condition and overexpress HER2 as compared to corresponding cells that are not involved in the pathologic condition. For example, the cells can be cancer cells that overexpress HER2 as compared to the level of HER2 expressed by normal cell counterparts to the cancer cells. In one embodiment, a method of stimulating an immune response in a subject against cancer cells that express HER2 is performed by administering a vaccine composition of the invention under conditions that result in the stimulation of an immune response by the vaccine composition against the HER2-expressing cells.

Stimulating an immune response in a subject using the vaccine compositions of the present invention can be used to either treat or prevent cancer, such as HER2 expressing cancer. When used to treat cancer, the vaccine composition is administered to a subject who has been diagnosed with cancer, in order to stimulate or increase an immune response against the cancer cells. The vaccine composition can be used as the sole method of treatment, or it can be combined with other methods of treating the cancer. Alternately, the vaccine composition can be administered to a subject who has not been diagnosed with cancer as a means of preventing or decreasing the likelihood of cancer development. In some embodiments, the subject being vaccinated has been characterized as being a subject having a high or increased risk of developing cancer, such as an HER2-expressing cancer. Subjects can be characterized as being at high or increased risk of developing an HER2-expressing cancer as a result of, for example, family history, genetic testing, or high exposure to cancer-causing environmental conditions. In some embodiments, the HER2 antigen is an antigen capable of generating a B-cell mediated immune response. A number of HER2 antigens have been identified that are capable of generating a B-cell-mediated immune response, in which antibodies are generated against the HER2 antigen. In this embodiment, vaccination provides active acquired immunity to a subject against HER2-expressing cancer. The immune system recognizes the plant virus particles linked to HER2 antigen as foreign, destroys them, and "remembers" the HER2 antigen through the generation of memory B cells. Memory B cells are a B cell sub-type that are formed within germinal centers following primary exposure to an antigen, and are important in generating an accelerated and more robust antibody-mediated immune response in the case of re-exposure to the antigen. Accordingly, when the immune system of a subject is exposed to HER2 antigen on cancer cells or cancer cell precursors, it is prepared to respond recognizing and destroying cells expressing or overexpressing the HER2 antigen before those cells can proliferate and form a tumor.

In some embodiments, the method further includes the step of ablating the cancer through additional methods of cancer treatment. The additional methods can be used before, concurrent with, or after administration of the vaccine composition. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, and administration of immunotoxins.

In some embodiments, the step ablating the cancer includes administering a therapeutically effective amount of an anticancer agent to the subject. Examples of anticancer agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-α, rapamycin, thapsigargin, and bikunin.

Another method of ablating cancer such as breast cancer that has been treated with a vaccine composition of the present invention is to conducting surgery to remove the cancer tissue (e.g., breast cancer tissue) from the subject. Types of surgery for breast cancer vary depending on the nature of the breast cancer, and include lumpectomy, partial or segmental mastectomy or quadrantectomy, simple or total mastectomy, radical mastectomy, and modified radical mastectomy. Appropriate surgeries for treating other types of HER2-expressing cancer are known to those skilled in the art.

Evaluation of Efficacy

In order to evaluate the efficacy of the HER2 antigen-presenting virus particles as vaccines, challenge studies can be conducted. Such studies involve the inoculation of groups of test animals (such as mice) with an HER2 antigen-presenting virus particle by standard techniques. Control groups comprising non-inoculated animals and/or animals inoculated with a commercially available vaccine, or other positive control, are set up in parallel. After an appropriate period of time post-vaccination, the animals are challenged with a cancer cells. Blood samples collected from the animals pre- and post-inoculation, as well as post-challenge are then analyzed for an antibody response and/or T cell response to the HER2 antigen. Suitable tests for the B and T cell responses include, but are not limited to, Western blot analysis and Enzyme-Linked Immunosorbent Assay (ELISA) assay. Cellular immune response can also be assessed by techniques known in the art, including monitoring T cell expansion and IFN-γ secretion release, for example, by ELISPOT to monitor induction of cytokines.

The animals can also be monitored for development of other conditions associated with infection with cancer including, for example, growing tumor size, and the like for certain cancer cell lines, survival is also a suitable marker.

Administration and Formulation

The vaccine composition can include a pharmaceutically acceptable carrier, which constitutes one or more accessory ingredients. The term "pharmaceutically acceptable", when used in reference to a carrier, is meant that the carrier, diluent or excipient must be compatible with the other ingredients of the formulation and not deleterious to the recipient thereof.

Pharmaceutically acceptable carriers useful for formulating vaccine compositions for administration to a subject are well known in the art and include, for example, aqueous solutions such as water or physiologically buffered saline or other solvents or vehicles such as glycols, glycerol, oils such as olive oil or injectable organic esters. An additional pharmaceutically acceptable carrier for plant virus particles is edible plant tissue, in particular edible plant tissue in which the virus particles are grown. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the therapeutic agent and on the route of administration of the composition, which can be, for example, orally or parenterally such as intravenously, and by injection, intubation, or other such method known in the art. The pharmaceutical composition also can contain a second (or more) compound(s) such as a diagnostic reagent, nutritional substance, toxin, or therapeutic agent, for example, a cancer chemotherapeutic agent.

The plant virus particles linked to an HER2 antigen of the invention can be incorporated within an encapsulating material such as into an oil-in-water emulsion, a microemulsion, a micelle, mixed micelle, a liposome, a microsphere, a polymeric nanoparticle, or other polymer matrix (see, for example, Gregoriadis, Liposome Technology, Vol. 1 (CRC Press, Boca Raton, Fla. 1984); Fraley, et al., Trends Biochem. Sci., 6:77 (1981), each of which is incorporated herein by reference).

Exemplary routes of administration include, but are not limited to, orally or parenterally, such as intravenously, intramuscularly, subcutaneously, intraperitoneally, intrarectally, intracisternally or, if appropriate, by passive or facilitated absorption through the skin using, for example, a skin patch or transdermal iontophoresis, respectively. Furthermore, the pharmaceutical composition can be administered by injection, intubation, orally or topically, the latter of which can be passive, for example, by direct application of an ointment, or active, for example, using a nasal spray or inhalant, in which case one component of the composition is an appropriate propellant. As mentioned above, the vaccine composition also can be administered to the site of a tumor, for example, intravenously or intra-arterially into a blood vessel supplying the tumor.

The total amount of a vaccine composition to be administered to a subject can be administered as a single dose, either as a bolus or by infusion over a relatively short period of time, or can be administered using a fractionated treatment protocol, in which multiple doses are administered over a prolonged period of time. One skilled in the art would know that the amount of plant virus particle linked to an HER2 antigen to treat or prevent cancer in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

It is understood that the effective dosage will depend on the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

Useful dosages can be determined by comparing their in vitro activity and the in vivo activity in animal models. Methods for extrapolation of effective dosages in mice, and other animals, to humans are known in the art. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the vaccine composition vary depending upon many different factors, including means of administration, target site, physiological state of the patient, whether the patient is human or an animal, other medications administered, and whether treatment is prophylactic or therapeutic.

Kits

The present invention additionally provides for pharmaceutical kits or packs containing a vaccine composition of the invention. Individual components of the kit can be packaged in separate containers, associated with which, when applicable, can be a notice in the form prescribed by a governmental agency regulating the manufacture, use or sale of pharmaceuticals or biological products, which notice reflects approval by the agency of manufacture, use or sale for human or animal administration.

The kit can optionally further contain one or more other therapeutic agents for use in combination with the immunopotentiating composition of the invention. The kit may optionally contain instructions or directions outlining the method of use or administration regimen for the vaccine composition and/or additional therapeutic agents.

When one or more components of the kit are provided as solutions, for example an aqueous solution, or a sterile aqueous solution, the container means may itself be an inhalant, syringe, pipette, eye dropper, or other such like apparatus, from which the solution may be administered to a subject or applied to and mixed with the other components of the kit.

The components of the kit may also be provided in dried or lyophilized form and the kit can additionally contain a suitable solvent for reconstitution of the lyophilized components. Irrespective of the number or type of containers, the kits of the invention also may comprise an instrument for assisting with the administration of the composition to a patient. Such an instrument may be an inhalant, syringe, pipette, forceps, measured spoon, eye dropper or similar medically approved delivery vehicle.

The following example is included for purposes of illustration and is not intended to limit the scope of the invention.

EXAMPLE

Example 1: Presentation of HER2 Epitopes Using a Filamentous Plant Virus-Based Vaccination Platform Human epidermal growth factor receptor 2 (HER2)-positive cancers are aggressive, have poor prognoses, and have a high rate of metastasis and relapse. Immunotherapy (e.g. trastuzumab) has shown improvement in the outcome for HER2 patients. Development of drug resistance and short half-lives limiting the duration of the therapy are barriers in the development of effective therapeutic strategies. Furthermore, while passive immunotherapy provides treatment, it does not reduce the risk of recurrence of the disease. These barriers have fueled the development of active immunotherapies using HER2 vaccines. The inventors turned toward the development of a virus particle-based peptide vaccine. Specifically, HER2 epitopes were integrated on the plant-produced vaccination platform potato virus X (PVX) to overcome immunological tolerance against HER2. The carrier acts as an adjuvant and improves stability and B cell presentation of the epitopes Immunizations of FVB/N mice resulted in the production of HER2-specific antibodies, as shown by ELISA and confocal microscopy using HER2-positive human cancer cell lines.

Materials and Methods

PVX Propagation and Purification:

PVX was propagated in *Nicotiana benthamiana*. Leaves were harvested 10-14 days after mechanical inoculation with 5 μg of purified PVX particles. To purify the VNPs, 100 g of leaf tissue was homogenized in a standard blender using two volumes of cold 0.5 M borate buffer (pH 7.8) and the homogenate was filtered through 2-3 layers of cheesecloth. The pH was adjusted to 6.5 with 1 M HCl and the filtered homogenate was supplemented with 0.2% (w/v) ascorbic acid and 0.2% (w/v) sodium sulfite before centrifugation at 5500×g for 20 min. The supernatant was collected and supplemented with 0.2 M NaCl and 8% (w/v) PEG8000, and the solution was centrifuged at 15,000×g for 15 min. The pellet was resuspended in 0.1% 2-mercaptoethanol and 0.5 M urea followed by centrifugation at 8000×g for 30 min. The supernatant was ultracentrifuged at 160,000×g for 3 h and the pellet resuspended in 5 mL buffer overnight at 4° C. The suspension was then ultracentrifuged in a 10-40% sucrose gradient at 100,000×g for 2 h. The light-scattering band was collected and dialyzed against 0.5 M borate buffer (pH 7.8). The virus concentration in plant extracts was determined by UV/visible spectroscopy ($\varepsilon_{PVX}$=2.97 mL mg$^{-1}$ cm$^{-1}$).

Bioconjugation of P4 Peptide to PVX:

Cysteine-terminated P4 peptide with intervening glycine linker, PESFDGDPASNTAPLQP-GGG-C (SEQ ID NO: 2) was custom made at Cleveland Clinic Molecular Biology Core Laboratory (Cleveland, Ohio). P4 peptide was conjugated to the surface lysines on PVX coat proteins via a heterofunctional N-hydroxysuccinimide-PEG$_4$-maleimide linker (SM(PEG)$_4$) (Pierce Biotechnology, Inc., Rockford, Ill.) in a two-step reaction. Purified PVX at a concentration of 2 mg mL$^{-1}$ in 0.1 M potassium phosphate buffer (pH 7.0) was incubated with 10,000 molar excess of SM(PEG)$_4$ in the presence of 10% (v/v) final concentration of DMSO (Fisher Bioreagents) and incubated for two hours at room temperature, with agitation. The reaction was purified using 10 kDa cut-off centrifugal filtration (Millipore Billerica, Mass.) Immediately following the purification, PVX-SM(PEG)$_4$ conjugates at a concentration of 2 mg mL$^{-1}$ in 0.1 M potassium phosphate buffer (pH 7.0) were mixed with 5000 molar excess of P4 peptide and incubated overnight with agitation. Post-incubation, PVX-P4 was purified using 10 kDa cut-off centrifugal filtration. Successful conjugation of P4 to PVX was confirmed using denaturing SDS gel electrophoresis. Protein samples were analyzed on 4-12% NuPage gels (Life Technologies, Grand Island, N.Y.) in 1×MOPS SDS running buffer (Life Technologies, Grand Island, N.Y.). Protein bands were visualized under white light after staining with GelCode Blue Stain Reagent (Pierce Biotechnology, Inc., Rockford, Ill.). Structural integrity of PVX post conjugation was ascertained using TEM imaging and FPLC size exclusion liquid chromatography. Diluted PVX-P4 samples (10 μL, 0.1 mg mL$^{-1}$) were negatively stained with 2% (w/v) uranyl acetate for 2 min on a carbon-coated copper grid. Samples were analyzed using a Zeiss Libra 200FE transmission electron microscope at 200 kV. The elution profile of purified PVX-P4 was compared with that of PVX by FPLC using a Superose6 column and Akta Purifier (GE Healthcare Life Sciences, Piscataway, N.J.).

Immunization of Mice:

Female FVB/N mice (n=3/group) were immunized subcutaneously with formulations consisting of either PVX-P4 (10 μg versus 100 μg, corresponding to 0.3 and 3 μg P4, respectively), PVX (10 μg versus 100 μg) or P4 peptides (0.3 and 3 μg P4) suspended in PBS with 35 μl GERBU adjuvant (Gerbu Biotechnik, Heidelberg, Germany) while maintaining total injection volume of 100 μl. The vaccination schedule was based on earlier studies. Jasinska et al., Int J Cancer, 107:976-83 (2003). Specifically, mice were vaccinated four times—every third week in a 63-day period. Each vaccination was followed up by 5 days of intraperitoneal (I.P.) administration of recombinant interleukin-12 (IL-12) (Novus Biologicals, Littleton, Colo.) starting from the third day of vaccination. 50 ng and 100 ng IL-12 in PBS containing 0.1% mouse serum albumin (Sigma, St. Louis, Mo.) was administered following the first two and last two rounds of injections, respectively. Blood serum was collected prior to the first vaccination and seven days after the last booster injection by bleeding mice through the retro-orbital plexus. Blood was collected in Greiner Bio-One VACUETTE™ MiniCollect™ tubes (Thermo Fisher Scientific, Waltham, Mass.) and centrifuged at 14,800 rpm for 10 min to separate the serum, which was then stored at 4° C. until analyzed. All mice were euthanized after the last blood collection.

Enzyme-Linked Immunosorbent Assay (ELISAs):

ELISAs were carried out to determine specificity of antisera from FVB/N mice immunized with PVX-P4, PVX and P4 against the immunogens as well as HER2 protein and to estimate immunoglobulin isotypes in the antisera. 96-well Nunc Polysorp Immuno plates (Thermo Fisher Scientific, Waltham, Mass.) were coated with 1 μg PVX/well or 1 μg PVX-P4/well in coating buffer (0.05 M Na$_2$CO$_3$, 0.05 M NaHCO$_3$, 0.015 M NaN$_3$ in dH$_2$O, pH 9.6) and incubated overnight at 4° C. After coating, wells were blocked using 200 mL/well blocking buffer (2.5% (w/v) milk, 25% (v/v) FBS in 1×PBS, pH 7.4) at 37° C. for 1 hour. After blocking, 1:100 μL sera (in blocking buffer) were added to the wells and incubated at 37° C. for 2 hours. After serum incubation, 100 μL of alkaline phosphatase-labeled goat anti-mouse IgG (Life Technologies, Grand Island, N.Y.) at 1:3,000 (in blocking buffer) was added to each well and incubated at 37° C. for 1 hour. In between each step, plates were washed four times with washing buffer (0.1% (v/v) Tween-20 in PBS, 200 μL/well). Wells were developed by adding 100 μL of 1-step PNPP substrate (Thermo Fisher Scientific, Waltham, Mass.) for 10 min at 4° C. Reaction was stopped using 100 μL of 2M NaOH. Absorbance was read at 405 nm using a Tecan microplate reader. Similarly, 96-well maleimide activated plates (Pierce, Rockford, Ill.) were coated with 0.3 μg P4-cys peptide/well in binding buffer (0.1 M sodium phosphate, 0.15 M sodium chloride, 10 mM EDTA, pH 7.2) and incubated for 2 hours at room temperature. Wells were then washed three times with washing buffer (0.05% (v/v) Tween-20 in PBS, 200 μL/well) Immediately before use, wells were incubated with 200 μL of 10 μg/mL cysteine solution for 1 hour at room temperature to inactivate excess maleimide groups. After washing with the wash buffer thrice, mice sera at 1:100 dilution in binding buffer was added and incubated for 1 hour at room temperature and then washed thrice. After serum incubation, 100 μL of alkaline phosphatase-labeled goat anti-mouse IgG (Life Technologies, at 1:3,000 in blocking buffer) was added to each well and incubated at 37° C. for 1 hour. Wells were developed by adding 100 μL of 1-step PNPP substrate (Fisher) for 10 minutes at 4° C. Reaction was stopped using 100 μL of 2M NaOH. Absorbance was read at 405 nm as described earlier. HER2 specificity of the antisera (1:100 dilutions) from mice immunized with PVX, PVX-P4 and P4 was determined similarly using plates coated with 1 μg HER2 protein/well. Determination of IgG isotypes in the PVX-P4 injected mice was carried out using similar ELISA experiments, whereby pooled pre-vaccination and post-vaccination mice sera (1:100 dilutions) from the PVX-P4 injected mice were incubated on maleimide activated plates (Pierce) coated with 0.3 μg peptide P4-cys/well. Following the incubation, anti-mouse IgG2a-alkaline phosphatase antibody, anti-mouse IgG2b-alkaline phosphatase antibody and anti-mouse IgG1—alkaline phosphatase conjugated antibodies (all from Novus Biologicals, Littleton, Colo.) at 1:1000 dilutions were added to the wells and incubated for 1 hour at 37° C. Following this, the wells were developed and analyzed as described earlier.

Cell-Binding Assay:

SK-BR-3 cells (ATCC) and MCF-7 cells (ATCC) were maintained on McCoy's 5A media and DMEM media supplemented with 10% (v/v) fetal bovine serum and 1% (v/v) Penicillin/Streptomycin (all reagents from Life Technologies, Grand Island, N.Y.) at 37° C. and 5% $CO_2$. For the cell-binding assay, 25,000 SK-BR-3 or MCF-7 cells per well were cultured onto glass coverslips in a 24-well suspension culture plate for 24 hours. After washing and replacing with fresh media, pooled antisera from PVX-P4 and PVX vaccinated mice were added into the culture media (1:250 dilutions) and incubated with cells for 3 h. A rabbit anti-human HER2 Ab (ACROBiosystems, Newark, Del.) was used as a positive control. Post-incubation, cells were washed thrice with sterile saline and fixed for 5 min at room temperature with DPBS containing 4% (v/v) paraformaldehyde and 0.3% (v/v) glutaraldehyde. Cells were permeabilized with 0.2% Triton-X 100 (Fisher Bioscience) for 2 min PVX-P4 and PVX antisera treated cells were stained with goat anti-mouse-Alexa Fluor 488 secondary antibody (1:500 dilutions) (Life Technologies) with 5% goat serum while HER2 antibody treated cells were stained with goat antirabbit Alexa Fluor 488 secondary antibody (1:500) (Life Technologies, Grand Island, N.Y.) for 60 min at room temperature. Cells were washed thrice with DPBS. As negative control, cells were similarly reacted with secondary antibodies without a primary antibody or antisera treatment. All coverslips were then mounted onto glass slides using Fluoroshield with DAPI mounting media (Sigma, St. Louis, Mo.) resulting in nuclear staining and sealed using nail polish. Confocal images were captured on Olympus FluoView™ FV1000 LSCM and data processed using ImageJ 1.44o software.

Results and Discussion

Figure 2:
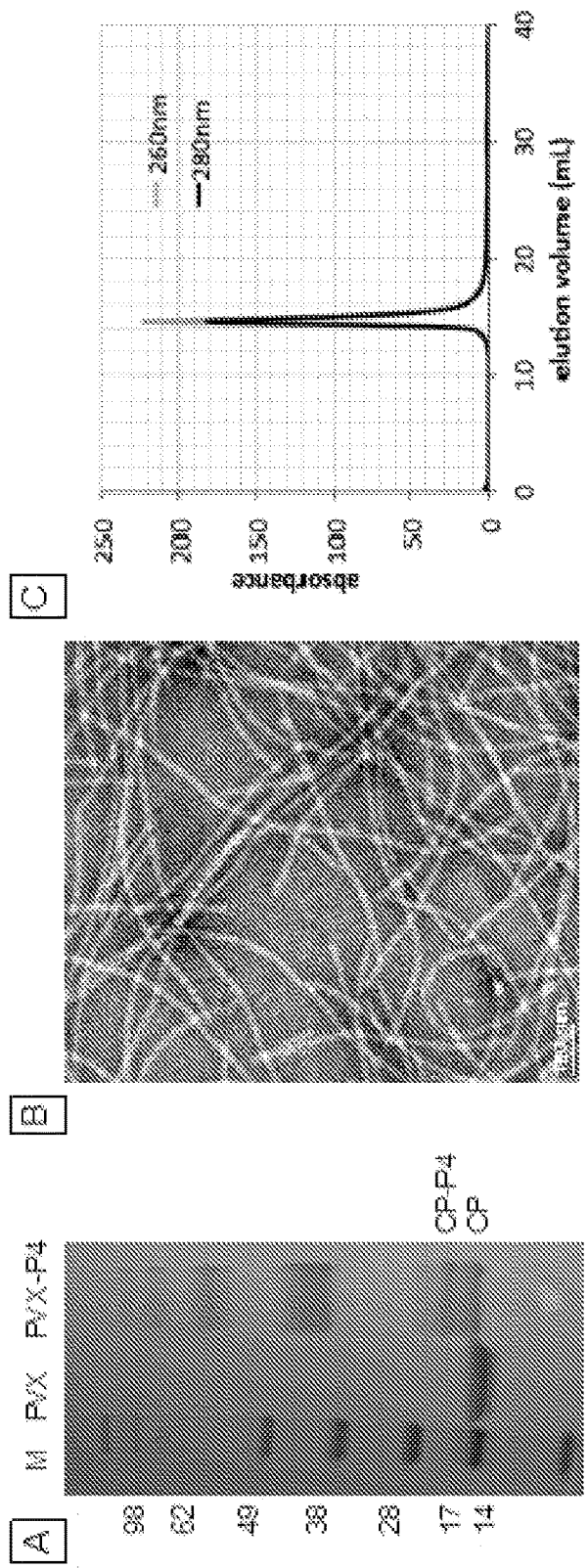
FIG. 2 (A-C) provides an image showing the characterization of PVX-P4 filaments. A) SDS-PAGE after Coomassie blue staining of PVX and PVX-P4. SeeBlue Plus2 was used as a molecular weight marker (M); numbers on the left indicate the molecular weights in kDa. The PVX CP band appears at ~15 kDa and the modified CP-P4 band at ~17 kDa; the P4 sequence PESFDGDPASNTAPLQP-GGG-C (SEQ ID NO: 2) has a molecular weight of ~2 kDa. Density analysis using ImageJ software and band analysis tool indicate a ratio of ~1:1 CP:CP-P4, or ~50% of CP-P4. B) TEM of PVX-P4 negatively stained with 2% (w/v) UAc confirms structural integrity of the filamentous particles. C) FPLC of PVX-P4 using a Superose6 column and Akta Purifier; the elution profile indicates that PVX-P4 is intact.

PVX was produced through farming in *N. benthamiana* plants using previously established protocols and extracted at yields of 20 mg of pure PVX from 100 grams of infected leaf material. Lee et al., Methods Mol Biol., 1108:3-21 (2014). The P4 epitope was chemically ligated to PVX using solvent-exposed lysine side chains. Steinmetz et al., Nano Lett., 10:305-12 (2010). Chemical conjugation was achieved using a cysteine-terminated P4 peptide with intervening glycine linker, PESFDGDPASNTAPLQPEQLQ-GGG-C (SEQ ID NO: 2), and a bi-functional N-hydroxysuccinimide-maleimide linker (sulfo-SMCC, Pierce). The reaction mixtures were purified by dialysis and final product characterized by SDS-PAGE, TEM, and FPLC (FIG. 2).

SDS-PAGE confirms the presence of higher molecular weight bands for PVX-P4 at ~17 kDa in addition to the PVX coat protein band at ~15 kDa; this increase in molecular weight is in good agreement with the size of P4, which has a molecular weight of ~2 kDa. Band density analysis using ImageJ software and band analysis tool indicate a ratio of coat protein (CP):P4-modified coat protein (CP-P4) of 1:1, or ~50% of CP-P4. PVX filaments consist of 1270 identical copies of a single CP; therefore PVX-P4 displays ~600 P4 epitopes per particle.

Gel electrophoresis also indicated multimeric coat proteins as higher molecular weight bands. While reactive cysteines have not been reported for the PVX coat protein, one cannot rule out that coat proteins may be interlinked through the bi-functional NHS-maleimide linker (targeting surface lysines and cysteines on the coat protein). Indeed, control experiments in which PVX and the NHS-maleimide linker were mixed and incubated (without the addition of the P4 peptide) resulted in a similar band pattern showing the high molecular weight bands (not shown). Nevertheless, interparticle crosslinking of the PVX-P4 formulation was not observed in TEM or FPLC (see below); therefore, it is likely that addition of the bivalent linker may trigger some intraparticle crosslinking.

TEM imaging and FPLC size exclusion chromatography confirm that PVX-P4 filaments remained structurally sound. Elongated filaments of approximately 515×13 nm were observed in TEM imaging, and the elution profile using a Superose6 column and Akta Purifier is consistent with intact PVX; broken filaments, free CPs or free P4 were not detected in any of the samples analyzed.

Female FVB/N mice (n=3/group) were immunized subcutaneously with formulations consisting of antigens at low doses and high doses suspended in PBS and Gerbu adjuvant: PVX (10 µg versus 100 µg), PVX-P4 (10 µg versus 100 µg), and free P4 at 0.3 versus 3 µg P4 peptide/mouse. The immunization schedule was modeled after previously published protocols (Wagner et al., Breast Cancer Res Treat, 106:29-38A (2007)) (FIG. 1). Recombinant mouse IL-12 was co-administered. IL-12 stimulates a Th1 response, which mediates an IgG class switch toward the complement-fixing IgG2a/b subtypes. Th1-biased response is desired because IgG2a/b induce stronger anti-tumor effects compared to IgG1 antibodies. Kim et al., Int J Cancer; 102:428-34 (2002). Blood was collected pre-immunization and seven days after the last immunization.

Figures 3A, 3B:
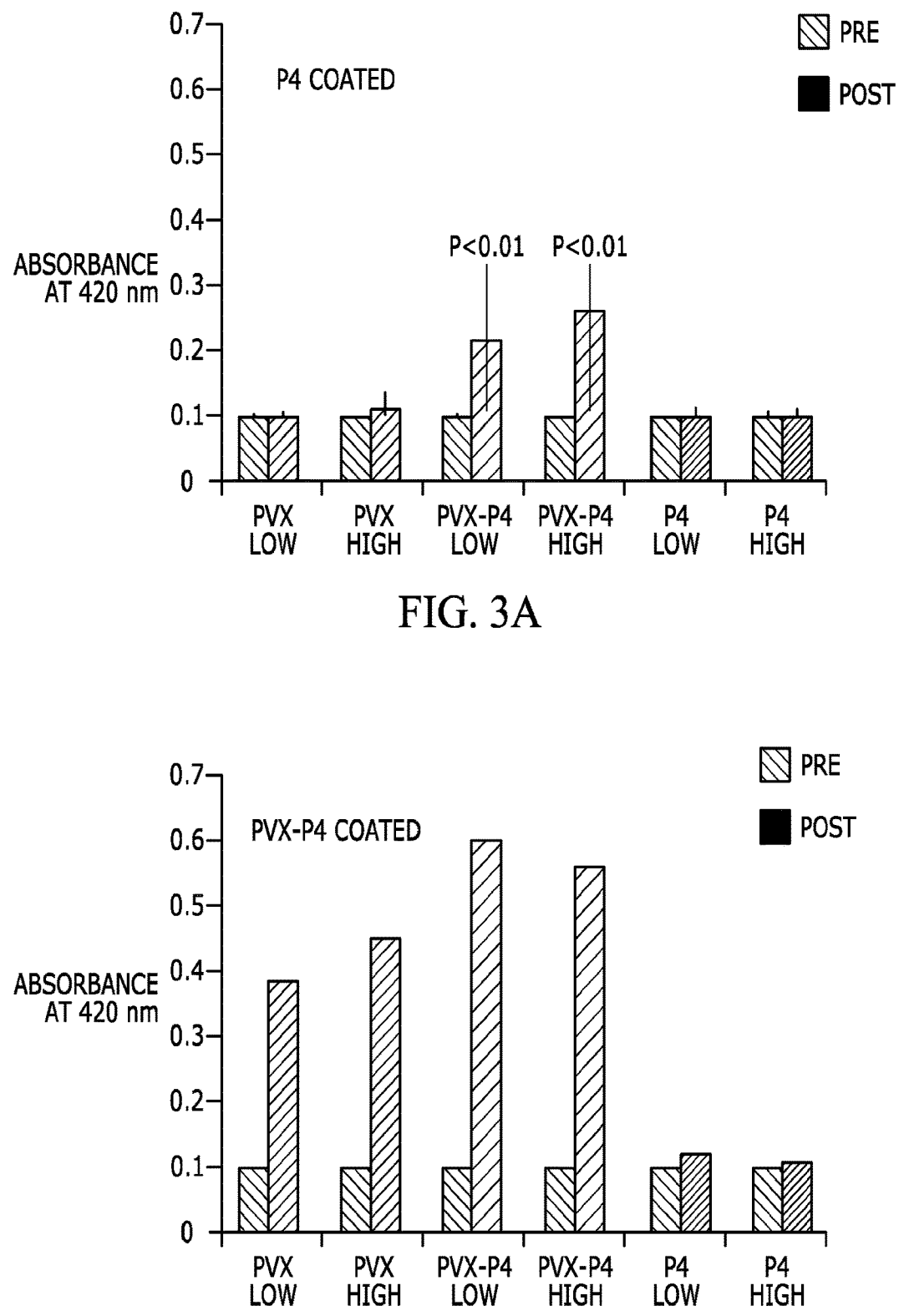
Figure 3C:
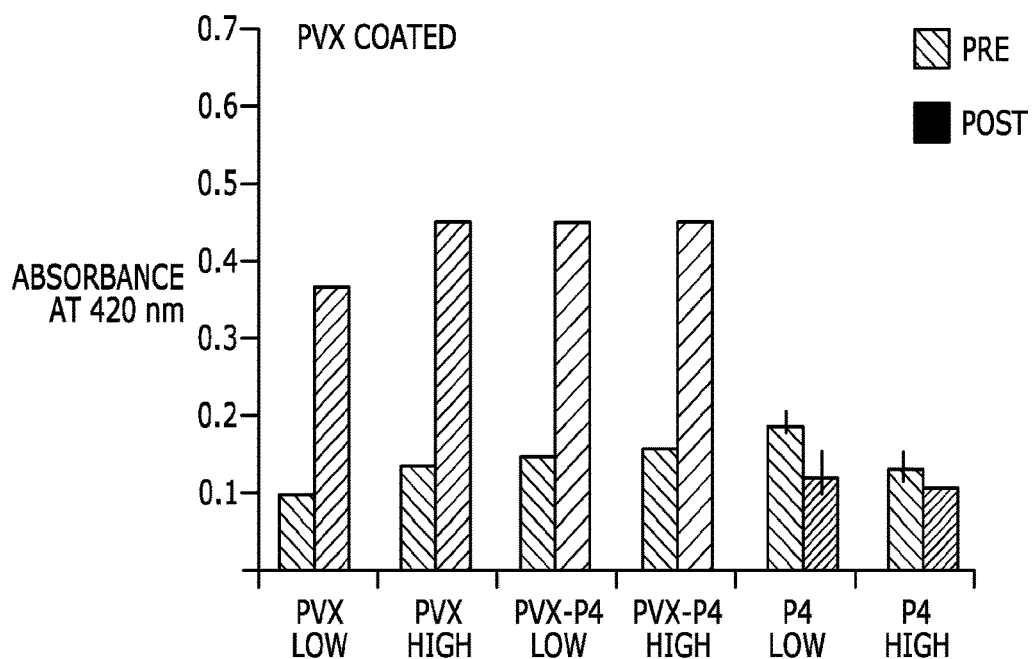
FIG. 3 (A-E) provides bar graphs showing ELISA results showing specificity of antisera from FVB/N mice immunized with PVX, PVX-P4, and P4 at low dose (0.3 μg P4 peptide) and high dose (3 μg P4 peptide). Sera at a 1:100 dilution were tested against P4 peptide (A), PVX-P4 (B), PVX (C), and HER2 protein (D); sera pre- (striped bars) and post-immunization (solid bars) were tested. E) IgG subtyping: plates were coated with HER2 protein and probed with sera pre- and post-immunization with PVX, PVX-P4, and P4; detection was carried out using secondary antibodies specific for IgG2a, IgG2b, and IgG1.

ELISA protocols were used to determine HER2-specific versus PVX-specific versus combinatorial HER2-PVX epitopes antibody titers (FIG. 3). Sera collected from mice immunized with PVX-P4 showed reactivity toward P4-, PVX-P4-, and PVX-coated plates indicating that both P4- and PVX-specific antibodies were produced at similar titers. Production or even pre-existence of carrier-specific antibodies has been reported for a number of virus-based presentation systems, including PVX. Uhde-Holzem et al., J Virol Methods, 166:12-20 (2010). Nevertheless, recent data indicate that induced or pre-existing carrier-specific immunity may not impair the effectiveness of the vaccination approach. Chuan et al., Biotechnol Bioeng, 110:2343-51 (2013). Control groups immunized with PVX showed similar levels of antibodies with specificity toward PVX.

Immunizations with free P4 peptide did not yield detectable antibody titers, underlying the need for the carrier. Indeed, earlier studies have highlighted the importance of organized and repeated displays of antigens on a carrier for effective B cell responsiveness. Bachmann et al., Science, 62:1448-51 (1993). Virus-based platforms such as PVX are excellent candidates for vaccine carriers due to their highly organized proteinaceous structures that promote B cell recognition, while their sizes are suitable for uptake by the antigen presenting cells (APCs) and lymph node trafficking. Reddy et al., Nat Biotechnol, 25:1159-64 (2007). Additionally, virus-based carriers also possess the ability to crosslink B cell receptors and could stimulate pattern recognition receptors, leading to an effective immune response directed against the displayed epitopes.

Figure 3D:
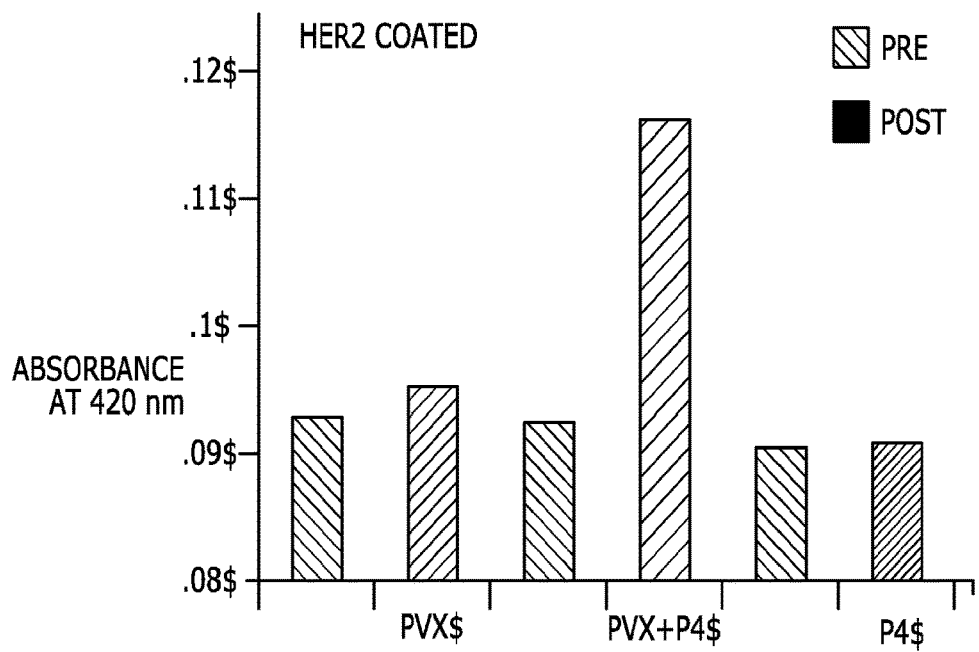
Figure 4:
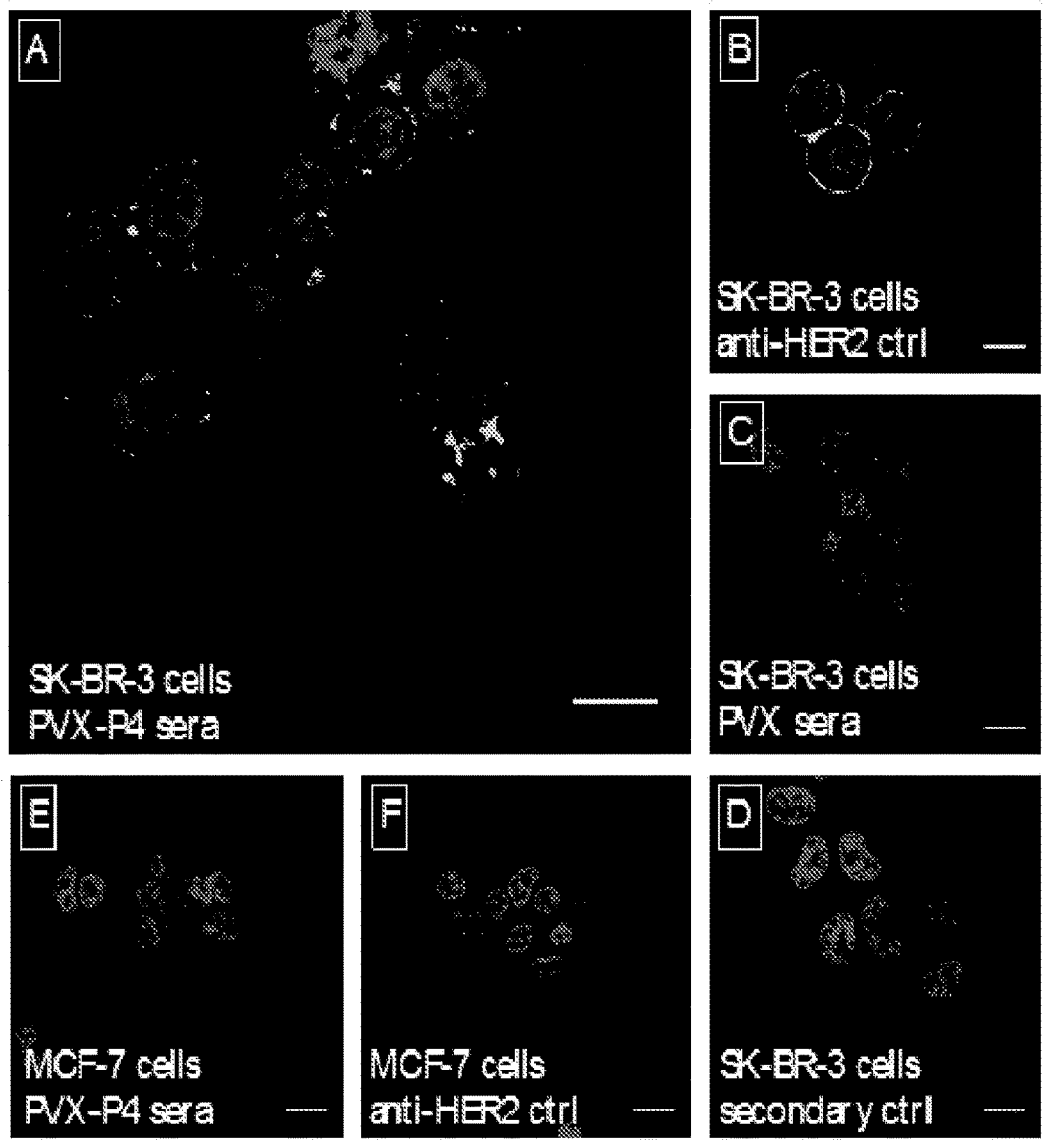
FIG. 4 (A-F) provides images showing PVX-P4 sera-cell interactions studied by confocal microscopy. HER2+ SK-BR-3 cells (A-D) and HER2- MCF-7 cells (E, F) were studied. Cells were exposed to sera (1:250 dilutions) from FVB/N mice immunized with PVX-P4 (A, E) or PVX (C), fixed, and stained with fluorescence-labeled anti-mouse secondary antibodies; cells stained with the secondary antibody only were used as control (D). Cells stained with an anti-HER2 antibody with fluorescence-labeled anti-mouse secondary antibodies served as positive control (B, E). Images were obtained using a Fluoview FV1000 (Olympus) microscope and images were analyzed using ImageJ software. The scale bars are 30 microns.

Next, the inventors determined and confirmed that sera from PVX-P4 immunized animals showed cross-reactivity toward HER2 protein, as shown by ELISA (FIG. 3D). This was further verified in cell imaging studies using human breast cancer cell lines: MCF-7 cells, which express negligible levels of HER2, and SK-BR-3 cells which are known to express high levels of HER2 (FIG. 4). PVX-P4 sera as well as anti-HER2 antibodies (positive control) stain HER2 protein on the surface of SK-BR-3 cells and do not show cross-reactivity with HER2-negative MCF-7 cells. Non-specific cell staining was not observed using sera from PVX-immunized animals or any other negative controls (FIG. 4). Immunofluorescence imaging confirmed that sera produced upon immunization with PVX-P4 yield antibodies that target HER2-positive breast cancer cells.

While it was found that P4-specific, and more importantly HER2-specific, antibodies were generated, the antibody titers observed were relatively low (detectable at a 1:100 dilution, FIG. 3). The HER2 epitope P4 conjugated to tetanus toxoid has been previously used in vaccination studies yielding strong immune responses, however, in those studies a higher dose of peptide was administered: 3 µg P4 peptide conjugated to PVX (this study) versus 25 µg P4 in previous studies. Jasinska et al., Int J Cancer, 107:976-83 (2003). Besides dosing, other factors could contribute to the antibody titers; these include the immunization schedule, route of administration, and use of adjuvants and/or other co-stimulatory molecules. Another consideration is the epitope presentation strategy: while this study used a chemical ligation to present linear epitopes conjugated to surface lysines, previous studies used genetically modified PVX displaying epitopes as amino-terminal coat protein fusions, which resulted in high antibody titers raised against the epitopes; for example see ref. Uhde-Holzem et al., Journal of virological methods, 166:12-20 (2010).

Figure 3E:
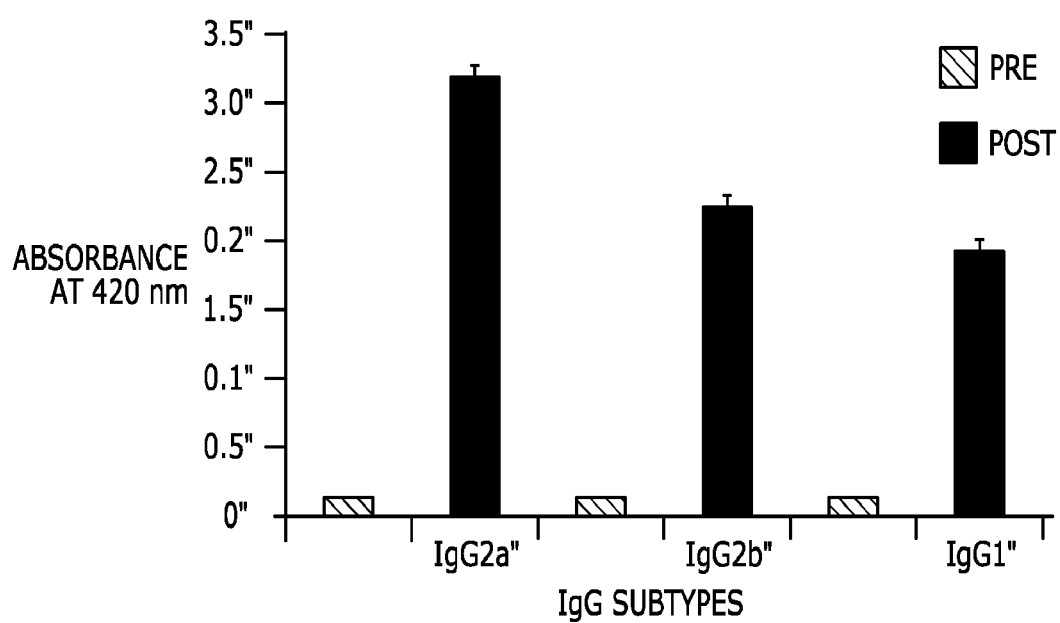

Antibody isotype profiling was carried out using pooled mouse sera from mice immunized with PVX-P4, and data indicate IgG2a>IgG2b>IgG1 levels (FIG. 3E). The segregation of IgG2 and IgG1 marks the Th1 vs. Th2 lymphocyte polarization and is desired for a cancer vaccine. IgG2a and IgG2b show stronger tumor inhibition through complement-dependent cellular cytotoxicity. Spiridon et al., Clin Cancer Res., 8:1720-30 (2002).

The differentiation of Th0 response is primarily dependent on the cytokine environment, with IL-12 production promoting Th1 commitment. Therefore, IL-12 administrations were included in the vaccination schedule. IL-12 stimulates differentiation of Th0 into Th1; furthermore IL-12 has also been reported to induce IFN-γ secretion, which in turn stimulates the expression of IgG2a over IgG2b and IgG1. Snapper C M, Paul W E., Science, 1987; 236: 944-7. Th1 bias therefore may be a result of IL-12 co-administration. However, it should be noted that a Th1 biased IgG response has been reported for T7 phage displaying HER2 CTL epitopes (Pouyanfard et al., PLoS One, 2012; 7:e49539) and a lambda phage-based peptide and gene delivery system (Thomas et al., Vaccine, 2012; 30:998-1008), suggesting such a bias could be an intrinsic property of the carrier particle. Future studies will investigate the mechanism of PVX-based vaccines.

Selective targeting of HER2-positive SK-BR-3 cells in combination with high titers of IgG2a/b indicates that the PVX-P4 formulation is a good candidate for further development and testing for applications as a therapeutic or prophylactic cancer vaccination platform.

CONCLUSIONS

In conclusion, the inventors prepared a PVX-based HER2 vaccination platform using the P4$_{378-394}$ epitope from the HER2 extracellular domain. While free P4 peptide immunization did not yield detectable HER2-specific antibodies, immunization with PVX-P4 formulations yielded HER2-specific IgG2a>IgG2b>IgG1 antibodies. These studies lay a foundation for the further development of plant virus-based cancer vaccines.

There are several advantages of plant virus particles over other display platforms. The plant virus-based PVX platform offers a multivalent platform with exceptional control over epitope density and placement. PVX-based vectors allow presentation of large proteins or combinations of peptides as coat protein fusions; this can be achieved through chemical bioconjugation or genetic engineering. For example, the inventors (Shukla et al., Biomaterials science, 2014; 2:784-97) and others (Oparka et al., Protoplasma, 1996; 189:133-41) demonstrated presentation of fluorescent proteins (>20 kDa) as amino-terminal coat protein fusions. Furthermore, recent data from our laboratory indicate that PVX has a natural tropism to target B cells, further supporting the choice of PVX as a vaccination platform. Shukla et al., Nanomedicine (Lond), 2014; 9:221-35.

Last but not least, PVX may enable the production of vaccines through molecular farming of edible plant tissue for implantation in underdeveloped countries, and therefore the proposed vaccine could make a global impact. Several plant viruses have been shown to accumulate at high titers in leaf tissue; scaled-up production of plant virus-based scaffolds with genetic epitope fusions in edible plant tissue thus may provide an attractive manufacturing platform for oral vaccines. Indeed, it has been shown that plant viruses withstand gastric conditions after oral administration, facilitating trafficking to the intestine following transport into the circulatory system. Rae et al., Virology, 343:224-35 (2005). Vaccination via the enteral route may also stimulate both mucosal and systemic immunity, therefore providing a higher level of protection.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A vaccine composition comprising a potato virus X particle linked to an HER2 antigen, wherein the HER2 antigen comprises an amino acid sequence of SEQ ID NO: 2.

2. The vaccine composition of claim 1, further comprising a pharmaceutically acceptable carrier.

3. The vaccine composition of claim 1, further comprising an adjuvant.

4. A method of treating or decreasing the risk of developing an HER2-expressing cancer in a subject, by administering to a subject in need thereof an effective amount of a vaccine composition comprising a potato virus X particle linked to an HER2 antigen, wherein the HER2 antigen comprises an amino acid sequence of SEQ ID NO: 2.

5. The method of claim 4, wherein the HER2-expressing cancer is breast cancer.

6. The method of claim 4, wherein the composition further comprises a pharmaceutically acceptable carrier.

7. The method of claim 4, wherein the composition further comprises an adjuvant.

8. The method of claim 4, wherein the vaccine composition is administered parenterally.

9. The method of claim 4, wherein the vaccine composition is administered orally.

10. A pharmaceutical kit comprising the vaccine composition of claim 1.

11. The vaccine composition of claim 1, wherein the potato virus X particle is conjugated to an HER2 antigen.

12. The method of claim 4, wherein the potato virus X particle is conjugated to an HER2 antigen.

* * * * *